(12) United States Patent
Liu et al.

(10) Patent No.: US 10,974,072 B2
(45) Date of Patent: Apr. 13, 2021

(54) COLLIMATOR, RADIOTHERAPY DEVICE AND CONTROL DRIVING METHOD THEREOF

(71) Applicant: OUR UNITED CORPORATION, Xi'an (CN)

(72) Inventors: Haifeng Liu, Xi'an (CN); Daliang Li, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 0 days.

(21) Appl. No.: 16/805,457

(22) Filed: Feb. 28, 2020

(65) Prior Publication Data
US 2020/0197727 A1    Jun. 25, 2020

Related U.S. Application Data

(63) Continuation of application No. PCT/CN2019/099397, filed on Aug. 6, 2019.

(30) Foreign Application Priority Data

Aug. 24, 2018 (CN) .......................... 2018 1 0971120

(51) Int. Cl.
*A61N 5/10*    (2006.01)

(52) U.S. Cl.
CPC ......... *A61N 5/1045* (2013.01); *A61N 5/1044* (2013.01); *A61N 5/1049* (2013.01); *A61N 2005/1052* (2013.01); *A61N 2005/1055* (2013.01); *A61N 2005/1094* (2013.01)

(58) Field of Classification Search
CPC .. A61N 5/1045; A61N 5/1044; A61N 5/1049; A61N 2005/1052; A61N 2005/1055; A61N 2005/1094
See application file for complete search history.

(56) References Cited

FOREIGN PATENT DOCUMENTS

| CN | 2258407 | 7/1997 | |
|----|---------|--------|---|
| CN | 2590600 | 12/2003 | |
| CN | 101195058 | 6/2008 | |
| CN | 109011217 | 12/2018 | |
| CN | 109011219 | 12/2018 | |
| CN | 109157762 | 1/2019 | |
| WO | 2012011083 A1 | 1/2012 | |
| WO | WO-2017020244 A1 * | 2/2017 | ........... A61N 5/1081 |

* cited by examiner

*Primary Examiner* — Kaylee R Wilson
(74) *Attorney, Agent, or Firm* — Brion Raffoul

(57) ABSTRACT

The present disclosure discloses a collimator, a radiotherapy device and a control driving method thereof, belonging to the medical technical field. The collimator is applied to a radiotherapy device, the radiotherapy device includes a plurality of radioactive sources, a plurality of collimating hole groups are arranged on the collimator, and an included angle of each collimating hole group in the longitudinal direction is within a preset included angle range. Each of the collimating hole groups includes a plurality of collimating holes, and beams emitted from the plurality of radioactive sources intersect at a common focus after passing through each collimating hole of the collimating hole group. The collimator, the radiotherapy device and the driving control method thereof can protect sensitive tissues and organs during treatment.

20 Claims, 15 Drawing Sheets

COLLIMATOR, RADIOTHERAPY DEVICE AND CONTROL DRIVING METHOD THEREOF

CROSS REFERENCE TO RELATED APPLICATIONS

111 The present disclosure is a continuation of international application No. PCT/CN2019/099397, filed on Aug. 6, 2019, which claims priority to the Chinese application No. 201810971120.4, filed on Aug. 24, 2018, both are hereby incorporated by reference in its entireties.

TECHNICAL FIELD

The present disclosure relates to the field of medical technologies, and more particularly, to a collimator, a radiotherapy device and a control driving method thereof.

BACKGROUND

With the development of medical technologies, radiation treatment is more and more widely used in the treatment of tumors.

The existing radiation treatment system for treating heads mainly includes a head gamma knife, which uses a natural isotopic radioactive source, cobalt-60, to emit gamma rays, and uses the radioactivity of the rays to kill tumor cells. However, the rays may also damage normal tissues or cells. In the related technologies, the existing head gamma knife includes 30 or 180 radioactive sources, beams are emitted by a plurality of radioactive sources from different directions and focus on a common focus, such that the common focus has the largest gamma-ray dose rate, whereas the beams emitted from each radioactive source cause less damage to the normal tissues or cells. In this way, an objective of killing the tumor cells while protecting the normal tissues or cells is achieved, thereby achieving tumor treatment effects.

However, in the treatment of head tumors, sensitive tissues and organs (such as the eyes and other important nerves) need to be avoided. In existing radiotherapy devices, radiation of the sensitive tissues and organs is avoided by adjusting a gamma angle for a patient, i.e., by adjusting an elevation angle of head.

The present disclosure provides a new implementation mode for protection of sensitive tissues and organs.

SUMMARY

The present disclosure provides a collimator, a radiotherapy device and a driving control method thereof, which can protect sensitive tissues and organs during treatment. The technical solutions are described as follows.

In one aspect, there is provided a collimator, which is applied to a radiotherapy device. The radiotherapy device includes a plurality of radioactive sources, a plurality of collimating hole groups are arranged on the collimator, and an included angle of each of the collimating hole groups in a longitudinal direction is within a preset included angle range.

Each of the collimating hole groups includes a plurality of collimating holes, and beams emitted from the plurality of radioactive sources intersect at a common focus after passing through each collimating hole of the collimating hole group.

In another aspect, there is provided a radiotherapy device, which includes a radioactive source apparatus. The radioactive source apparatus includes a source body and the collimator provided by the present disclosure, and the source body is provided with a plurality of radioactive sources.

The present disclosure provides a control driving method for a radiotherapy device. The method includes: obtaining at least one angle range of emitting beams; and driving the radiotherapy device to emit beams within the at least one angle range of emitting beams and to ensure the beams to intersect at a common focus.

The technical solutions provided by the present disclosure have the following beneficial effects.

The present disclosure provides a radiotherapy device. A plurality of radioactive sources are arranged on the radiotherapy device, a plurality of collimating hole groups are arranged on the collimator, and an included angle of each of the collimating hole groups in a longitudinal direction is within a preset included angle range. Each of the collimating hole groups includes a plurality of collimating holes, and beams emitted from the plurality of radioactive sources intersect at a common focus after passing through each collimating hole of the collimating hole group. The plurality of radioactive sources may be driven by the radiotherapy device to rotate along a central axis of the radiotherapy device, such that the radioactive sources can be turned off when passing through sensitive tissues or organs, and that the radioactive sources can be turned on by emitting beams from the collimating holes on the collimator when passing through normal tissues and organs. In this way, during the treatment of head tumors, the sensitive tissues and organs such as eyes can be protected from extra damage.

BRIEF DESCRIPTION OF THE DRAWINGS

To describe the technical solutions of the embodiments of the present disclosure more clearly, the accompanying drawings required for describing the embodiments will be briefly introduced below. Apparently, the accompanying drawings in the following description are merely some embodiments of the present disclosure. To those of ordinary skills in the art, other accompanying drawings may also be derived from these accompanying drawings without creative efforts.

DETAILED DESCRIPTION OF THE EMBODIMENTS

Detailed description of implementations of the present disclosure will further be made below with reference to drawings in order to make the above objectives, technical solutions and advantages of the present disclosure more apparent.

Figure 1:
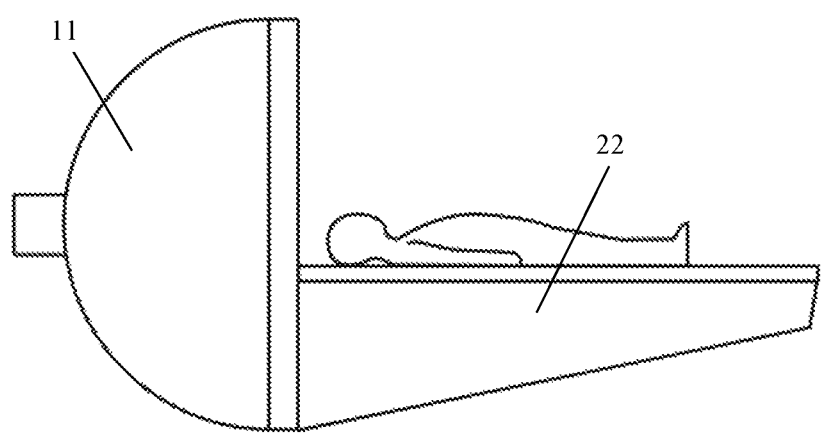
FIG. 1 is a schematic structural diagram of an existing radiotherapy device according to an embodiment of the present disclosure.
Figure 2:
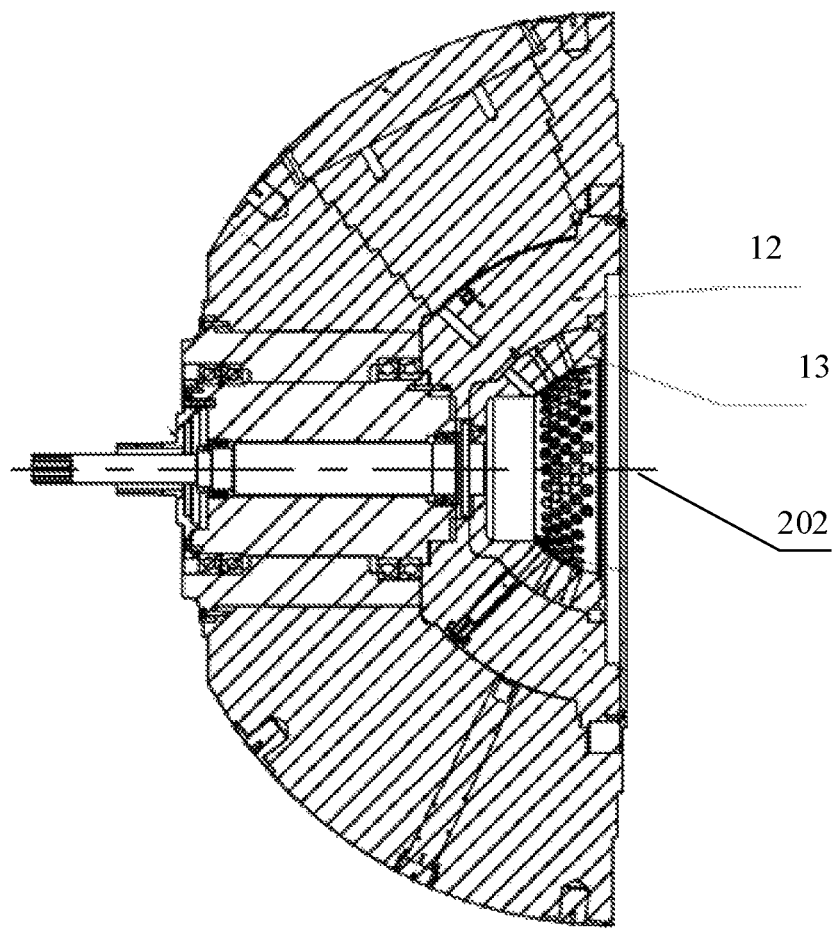
FIG. 2 is a schematic structural diagram of an existing radioactive source apparatus according to an embodiment of the present disclosure.

An existing radiotherapy device for treatment of head tumors is provided. Principles for radiation treatment of head tumors are as shown in FIG. 1 and FIG. 2. A plurality of radioactive sources may be mounted in a source body 12. Beams emitted from the plurality of radioactive sources intersect at a common focus after passing through a collimating hole on a collimator 13, and the common focus is located in a cavity of a radioactive source apparatus 11 of the radiotherapy device. A treatment couch 12 is used to carry a patient and to move the patient into a treatment cabin of the radioactive source apparatus 10, such that a nidus in the patient is located at the common focus for radiation treatment.

Figure 3:
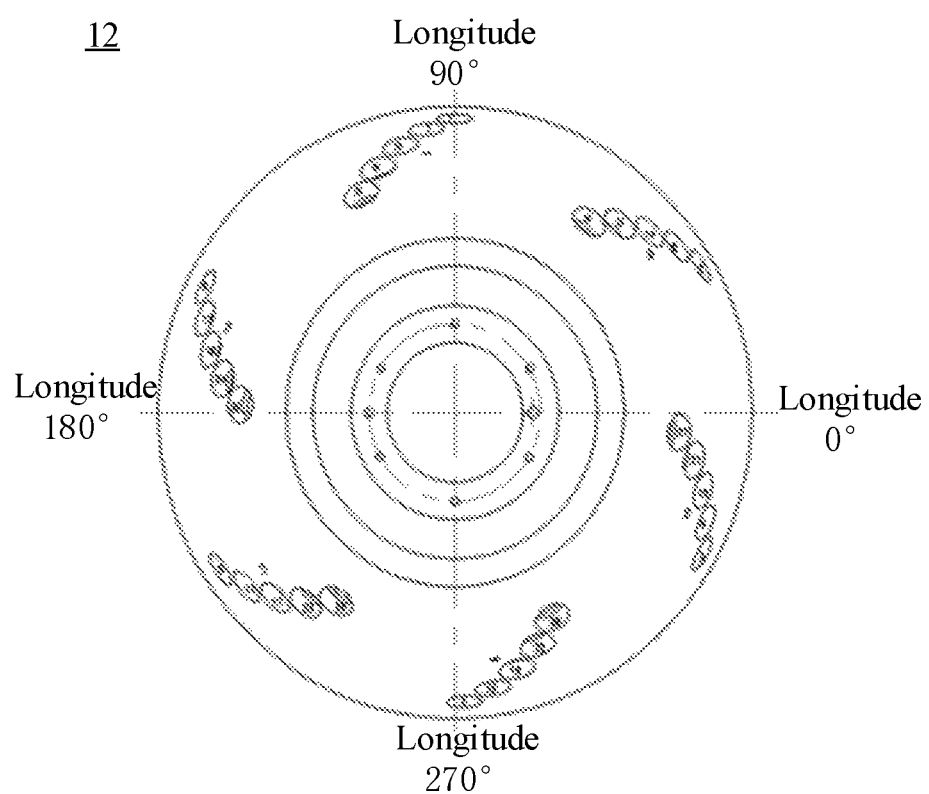
FIG. 3 is a schematic structural top view of an existing source body according to an embodiment of the present disclosure.
Figure 4:
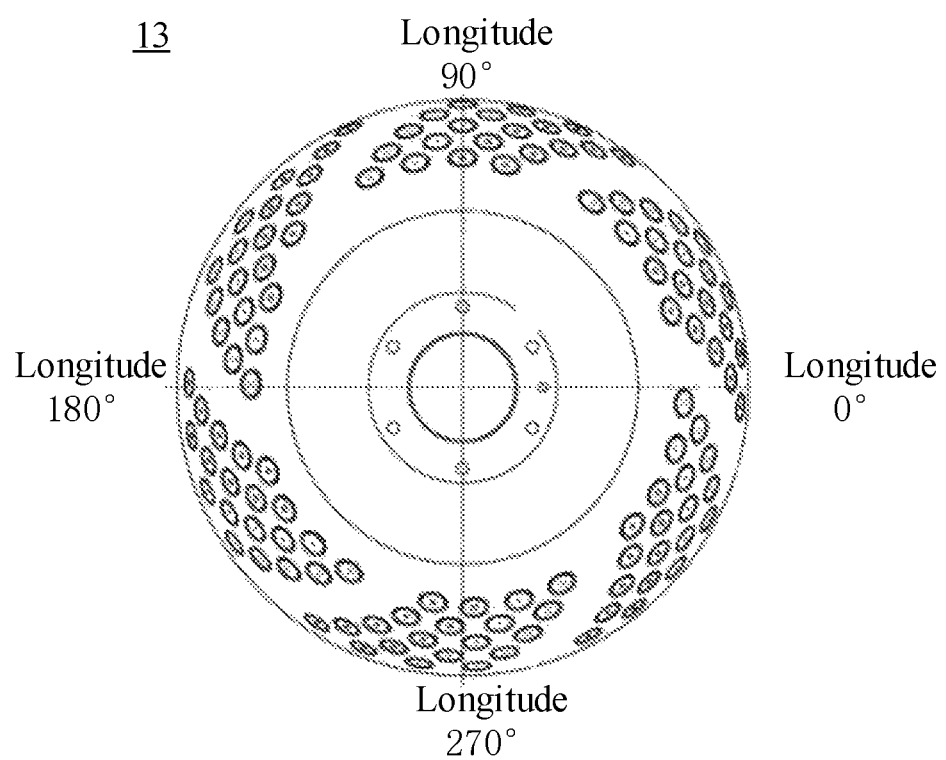
FIG. 4 is a schematic structural top view of an existing collimator according to an embodiment of the present disclosure.

The source body 12 of the existing radiotherapy device is bowl-shaped as shown in FIG. 3. The radioactive sources may be divided into six groups, wherein each group includes five radioactive sources, i.e., a total of 30 radioactive sources. The 30 radioactive sources are distributed on the source body. As shown in FIG. 4, the collimator 13 includes six collimation channel groups. The six collimation channel groups correspond to the positions of the six groups of radioactive sources. Each collimation channel group includes four subgroups. Collimating holes of one subgroup are filled with solid tungsten rods to implement off source shielding. The other subgroups each include five collimating holes, and the collimating holes in different subgroups have different sizes.

During treatment, the source body and the collimator may be driven to rotate with respect to each other to switch the collimating holes of different sizes and to implement on/off source by shielding the radioactive sources by the collimator. However, the six groups of collimating holes having different sizes and the on/off source are switched simultaneously, and one of the groups cannot be controlled individually. Therefore, during the treatment, a gamma angle needs to be adjusted, such that rays are kept away from sensitive tissues and organs such as eyes.

Figure 7:
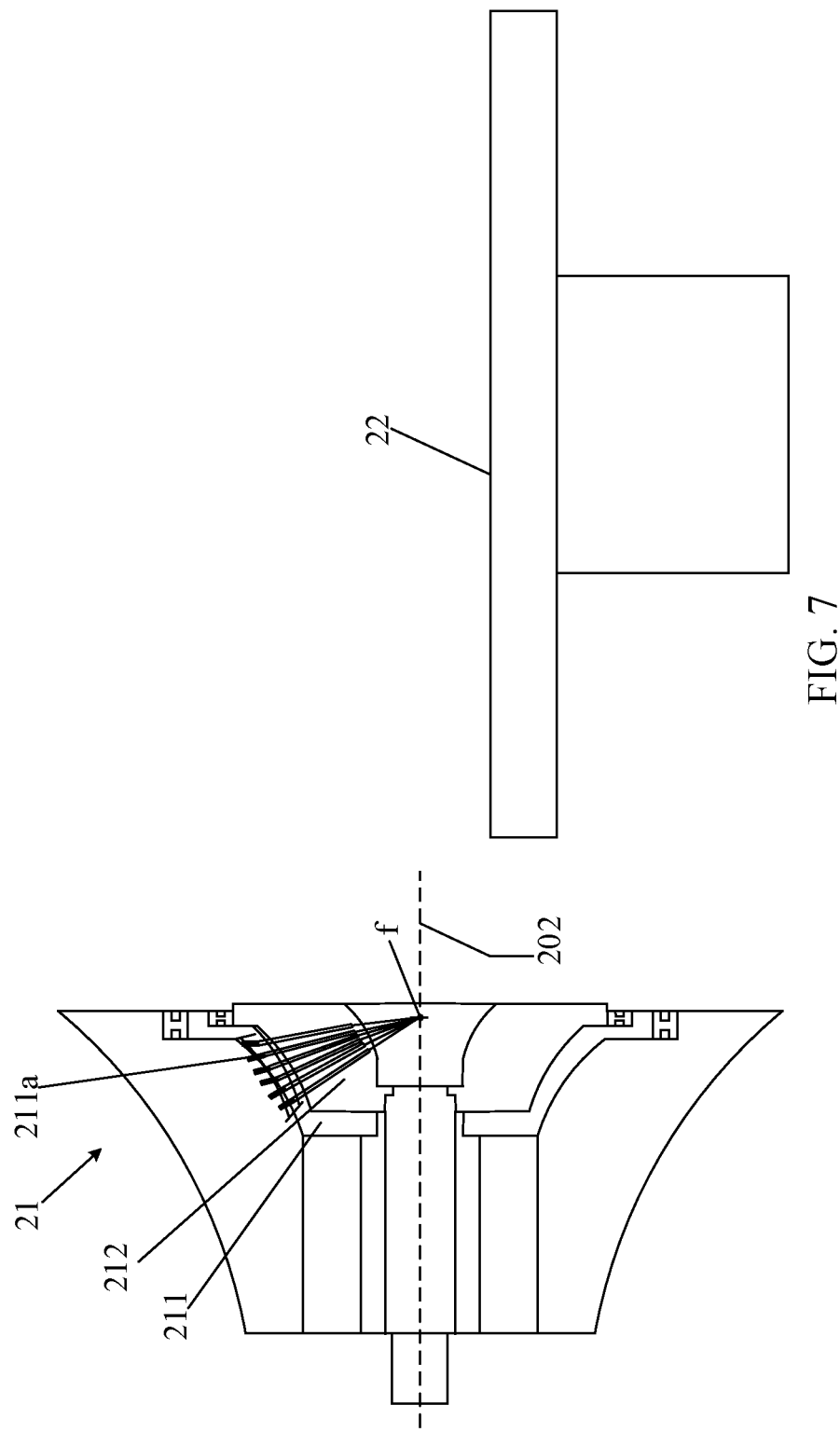
FIG. 7 is a schematic diagram of a radiotherapy device according to an embodiment of the present disclosure.
Figure 8:
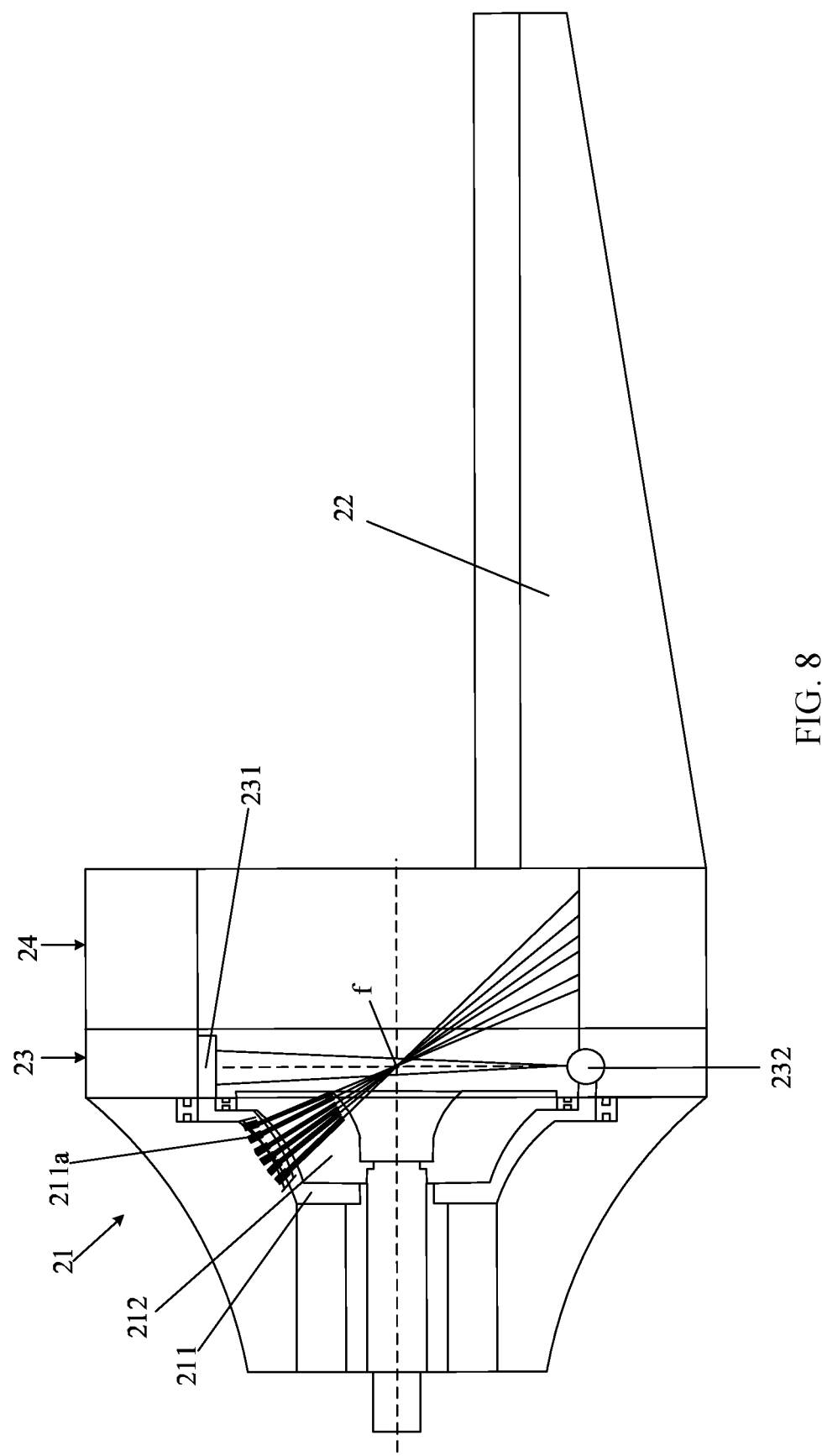
FIG. 8 is a schematic diagram of another radiotherapy device according to an embodiment of the present disclosure.

As shown in FIG. 7 and FIG. 8, the present disclosure provides a radiotherapy device, which includes a radioactive source apparatus 21. The radioactive source apparatus 21 includes a source body 211 and a collimator 212, the source body 211 is provided with a plurality of radioactive sources 211a, the collimator 212 is provided with a plurality of collimating hole groups, and an angle range of each of the collimating hole groups in a longitude direction is within a preset angle range. Each of the collimating hole groups includes a plurality of collimating holes, and beams emitted from the plurality of radioactive sources intersect at a common focus f on the central axis (202) after passing through each collimating hole of the collimating hole group.

Figure 5:
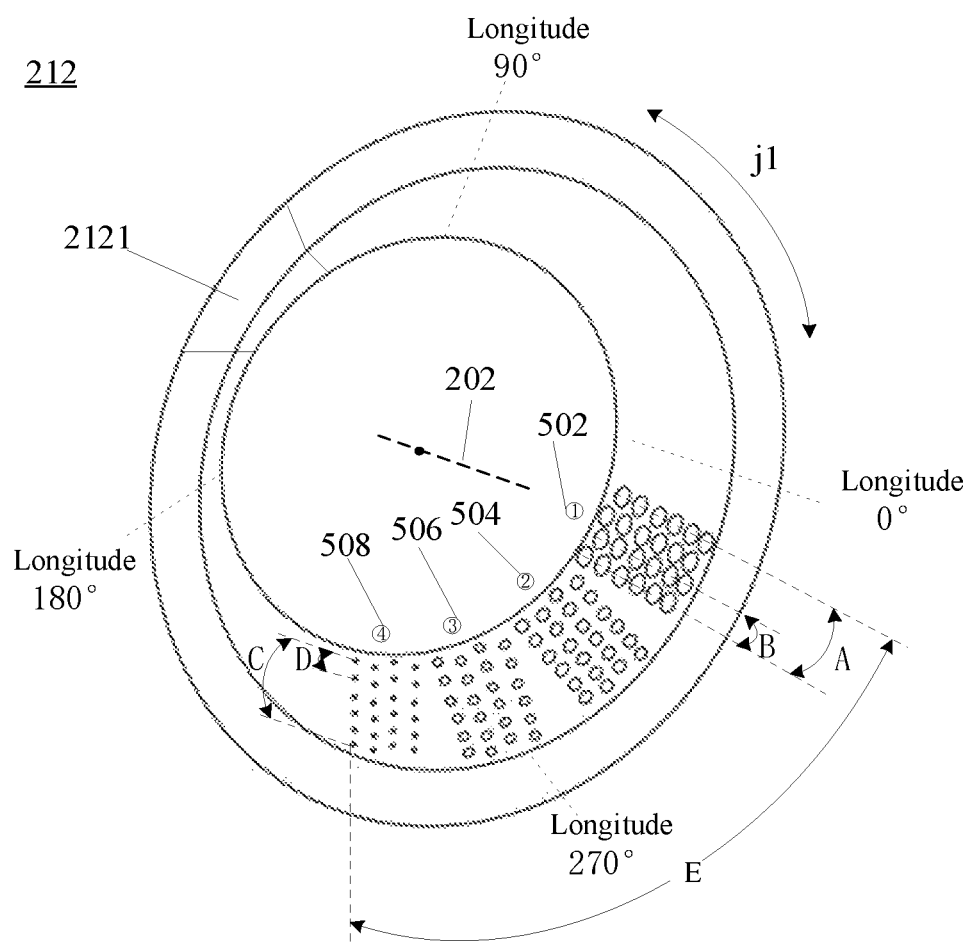
FIG. 5 is a schematic diagram of another collimator according to an embodiment of the present disclosure.
Figure 6:
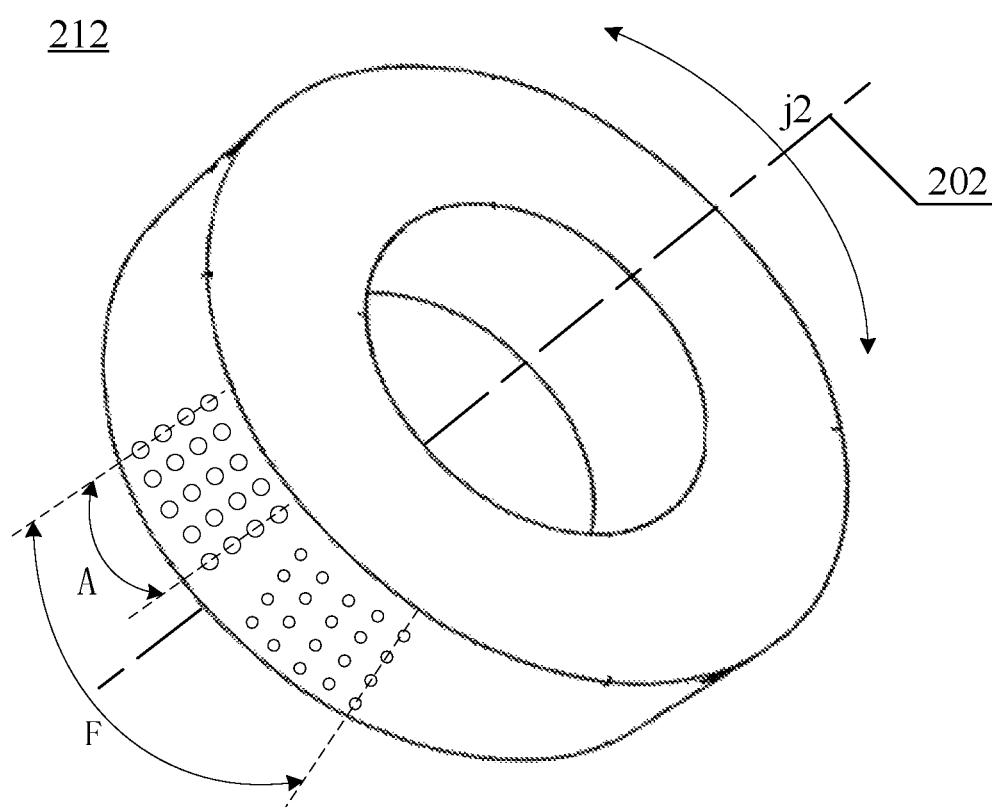
FIG. 6 is a schematic diagram of still another collimator according to an embodiment of the present disclosure.

For example, as shown in FIG. 5, the collimator 212 may be bowl-shaped, and the longitude direction of the collimator 212 is the circular direction, perpendicular to the central axis (202), as shown by arrow. 1 in FIG. 5, which is 0°-360° in the longitude direction. The collimator 212 may also be tube-shaped as shown in FIG. 6, and the longitude direction of the collimator 212 is the direction as shown by arrow j2 in FIG. 6. Both ends of a cylinder in FIG. 6 may have equal size, or of course, may have different sizes. The present disclosure does not limit the specific shape of the collimator, and the longitude direction in the present disclosure is described only by taking FIG. 5 and FIG. 6 as examples.

In the present disclosure, the angle range between the collimating hole groups in the longitude direction is within a preset angle range. The plurality of collimating hole groups in the longitude direction is within the preset maximum angle range E as shown in FIG. 5. In this example, all collimating hole groups are located within a portion of the collimator. More specifically, the collimating hole groups are located in a portion having the preset maximum angle range E less than 180° in the longitude direction. Moreover, in the present disclosure, as shown in FIG. 5, the angle range between the collimating bodies 212 in the longitude direction is an angle range formed by using centers of the collimating bodies 212 as a reference. It is to be noted here that if the collimating bodies include one row and the centers of the plurality of collimating bodies in the same row are located on the same longitude line, it is believed that the angle range between the plurality of collimating bodies in the longitude direction is zero degree. In the present disclosure, the preset angle range is greater than or equal to zero degree.

For example, as shown in FIG. 5, the present disclosure provides a collimator 212. The collimator 212 in FIG. 5 is provided with four collimating hole groups as an example, i.e., No. 1 collimating (502) hole group, No. 2 collimating (504) hole group, No. 3 collimating (506) hole group, and No. 4 collimating (508) hole group. Each collimating hole group includes 24 collimating holes respectively as an example. Taking the No. 1 collimating (502) hole group as an example, beams emitted from the plurality of radioactive sources intersect at a common focus after passing through each collimating hole of the No. 1 collimating (502) hole group. The angle range of the No. 1 collimating (502) hole group, the angle range of the No. 2 collimating (504) hole group, the angle range of the No. 3 collimating (506) hole group, and the angle range of the No. 4 collimating (508) hole group in the longitude direction are within a preset angle range. In FIG. 5, the No. 1 collimating (502) hole group is taken as an example, and the angle range of the No.

1 collimating (502) hole group in the longitude direction (the direction as shown by arrow j1 in FIG. 5) is denoted as A. As an example, the preset angle range A may be between 5° and 60°, i.e., 5°≤M≤60°. The preset angle range A may be any angle range between 5° and 60°. As an example, the preset angle range A may be 5°, 8°, 10°, 12°, 18°, 20°, 25°, 30°, 40°, 45°, 50°, or 60°. Reference may be made to other descriptions of the present disclosure for specific description of the collimator.

The collimator is provided with a plurality of collimating hole groups, which may mean that the collimator is provided with two or more collimating hole groups. In FIG. 5, an exemplary description is made by taking an example where the collimator 212 is provided with four collimating hole groups. Each collimating hole group includes a plurality of collimating holes, and the number of the plurality of collimating holes corresponding to the radioactive sources may range from 20 to 180, for example, 30 or 180. The present disclosure does not limit the number or arrangement of the collimating holes, and the example as shown in FIG. 5 merely serve as an exemplary description. The radiotherapy device also includes a plurality of radioactive sources. The collimating holes on the collimator correspond to the radioactive sources in number and arrangement, such that the beams emitted from the radioactive sources intersect at a common focus after passing through the collimating holes.

Figure 9:
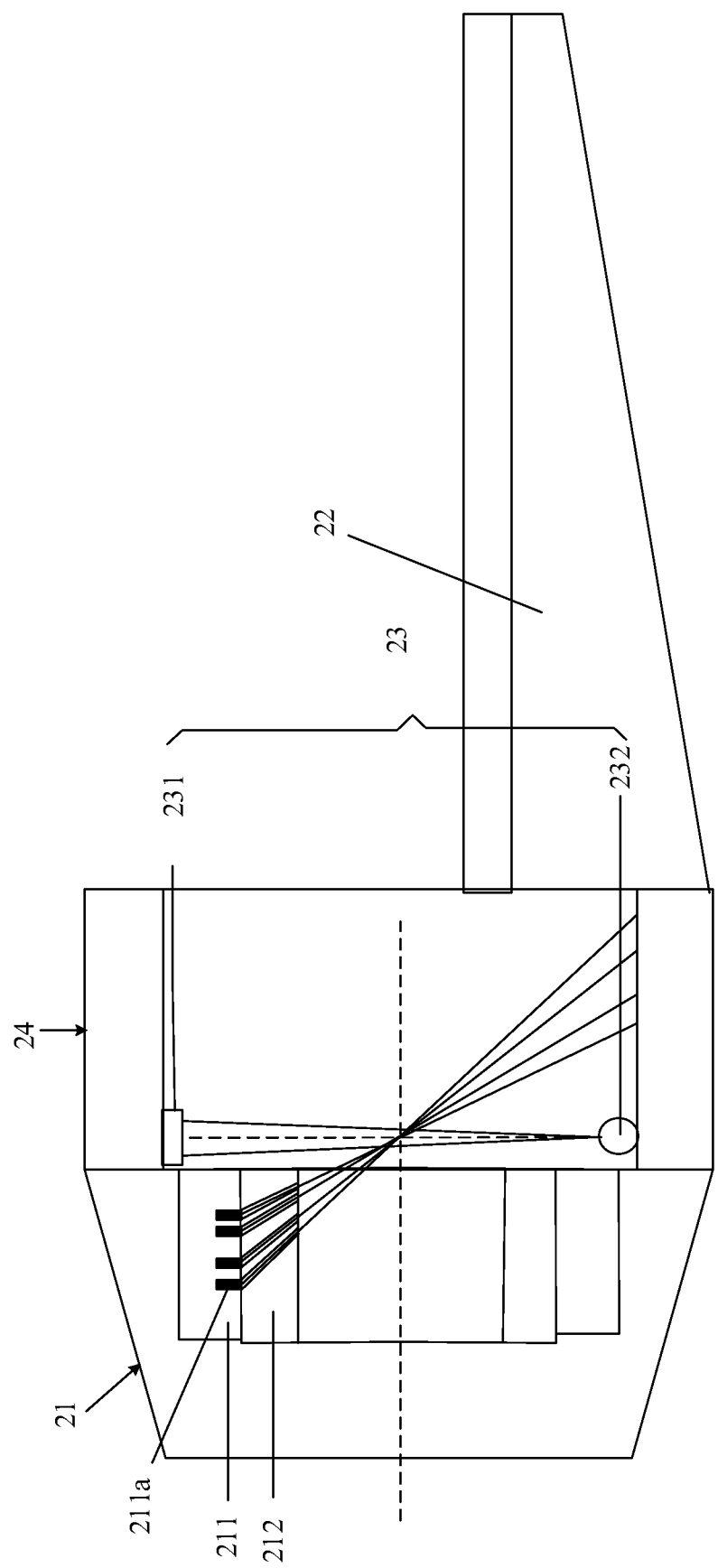
FIG. 9 is a schematic diagram of still another radiotherapy device according to an embodiment of the present disclosure.

For example, as shown in FIG. 6, the collimator 212 may also be tube-shaped as shown in FIG. 6, and the longitude direction of the collimator 212 is the circular direction, perpendicular to the central axis (202) as shown by arrow j2 in FIG. 6. In the example shown in FIG. 6, all collimating hole groups are located within a portion of the collimator. More specifically, the collimating hole groups are located in a portion having the preset maximum angle range F less than 90° in the longitude direction. Both ends of the cylinder in FIG. 6 may have equal size, or of course, may have different sizes (as shown in FIG. 9). The present disclosure does not limit the specific shape of the source body, and the shapes as shown in FIG. 5 and FIG. 6 are taken as examples. An exemplary description is made in FIG. 6 by taking an example where the collimator is provided with two collimating hole groups and each collimating hole group includes 20 collimating holes.

Figure 10:
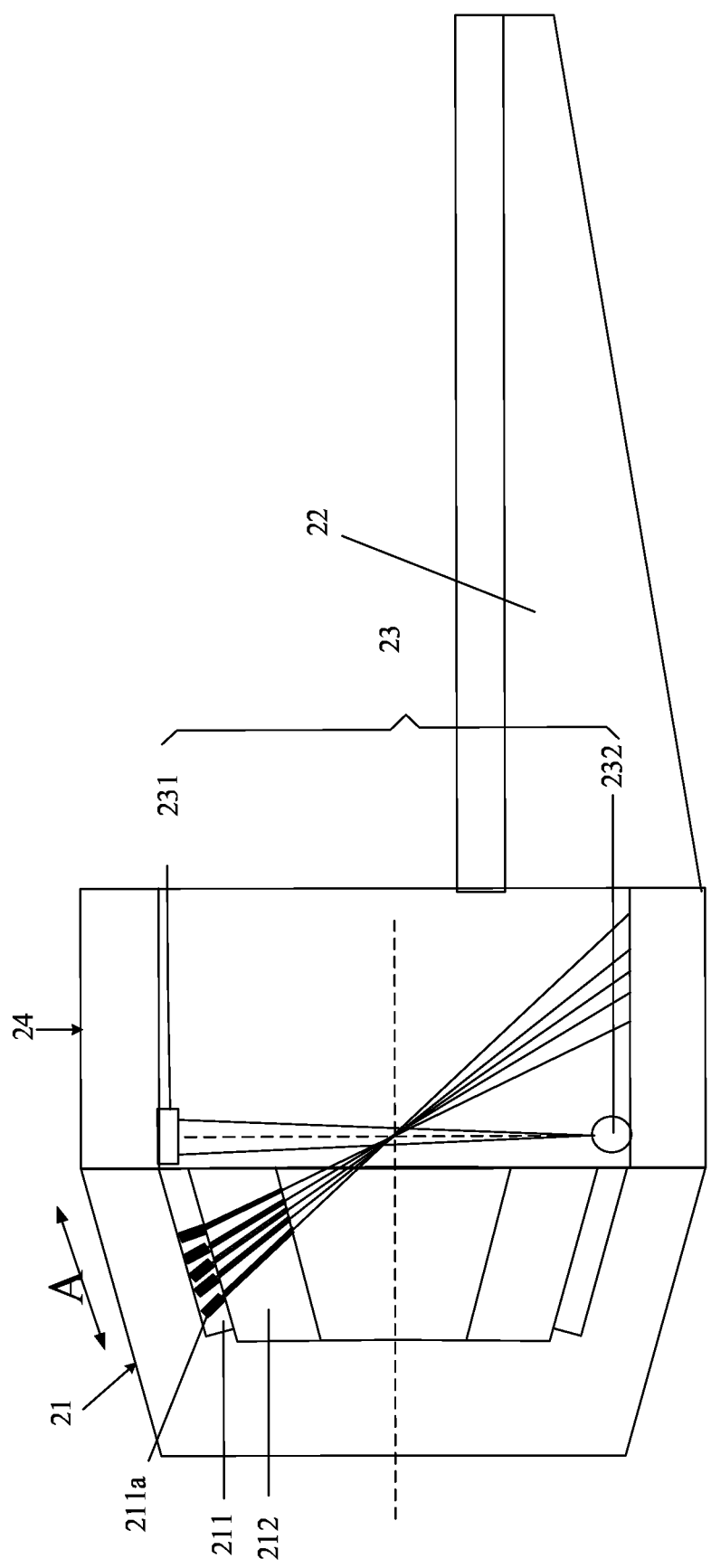
FIG. 10 is a schematic diagram of still another radiotherapy device according to an embodiment of the present disclosure.

As an example, in the radiotherapy device as shown in FIG. 9, the source body 211 is tube-shaped, and two ends of the tube-shaped source body 211 have equal diameter. In the radiotherapy device as shown in FIG. 9, the source body 211 and/or the collimator 212 may also move in a direction as shown by the central axis of the radioactive source apparatus 21 to implement on/off source. For example, in the radiotherapy device as shown in FIG. 10, the source body 211 is tube-shaped, and two ends of the tube-shaped source body 211 have unequal diameters. In the radiotherapy device as shown in FIG. 10, the source body 211 and/or the collimator 212 may also move in Direction A to implement on/off source. Of course, on/off source may be implemented through rotation, which is not limited in the present disclosure.

The present disclosure provides a radiotherapy device. A plurality of radioactive sources 211a are arranged on the radiotherapy device, a plurality of collimating hole groups are arranged on the collimator, and an angle range of each of the collimating hole groups in a longitude direction is within a preset angle range. Each of the collimating hole groups includes a plurality of collimating holes, and beams emitted from the plurality of radioactive sources 211a intersect at a common focus after passing through each collimating hole of the collimating hole group. The plurality of radioactive sources 211a may be driven by the radiotherapy device to rotate about a central axis of the radiotherapy device, such that the radioactive sources 211a can be turned off when passing through sensitive tissues or organs, and that the radioactive sources 211a can be turned on by emitting beams from the collimating holes on the collimator when passing through normal tissues and organs. In this way, during the treatment of head tumors, the sensitive tissues and organs such as eyes can be protected from extra damage.

In the radiotherapy device provided by the present disclosure, the radioactive source apparatus further includes a source body driving apparatus configured to drive the radioactive source to rotate about a central axis thereof. The driving apparatus may be a motor, and the radioactive source apparatus may also monitor the driving of the motor to obtain the relative position of the radioactive source in real time so as to determine whether to turn on or off the radioactive source.

During the treatment, a tumor of a patient may be accurately located at a common focus, such that tumor cells may be killed by radioactive rays. However, if the patient is moved during the treatment, the radioactive rays may deflect, which not only is disadvantageous to the treatment but also is harmful to health of the patient. The common focus of the existing radiotherapy device is located in a cavity of the radioactive source apparatus, and thus it is impossible to monitor whether the patient's head moves during the treatment. In the radiotherapy device provided by the present disclosure, the common focus is located outside an end surface of the radioactive source apparatus. For example, as shown in FIG. 8-FIG. 10, the common focus is located outside the end surface of the radioactive source apparatus, which is advantageous to observe and monitor whether the patient is moved during the treatment.

In the radiotherapy device provided by the present disclosure, the radiotherapy device also includes an imaging apparatus 23. The imaging apparatus 23 is arranged on a side of the radioactive source apparatus 21, and the common focus f is located within an imaging region of the imaging apparatus 23. That is, a tumor of a patient within the imaging region is imaged by the imaging apparatus 23, so to determine whether the patient is moved on the basis of the image. Displacement monitoring based on images has higher accuracy.

For example, the imaging apparatus 23 in the present disclosure may be any combination of one or more of an X-ray imaging apparatus, a CT (Computed Tomography) imaging apparatus, an MR (Magnetic Resonance) imaging apparatus, a DSA (Digital Subtraction Angiography) imaging apparatus, an ultrasound imaging apparatus, or a PET (Positron Emission Computed Tomography) imaging apparatus. For example, the imaging apparatus is the X-ray imaging apparatus. As an example, as shown in FIG. 8, the imaging apparatus may include an X-ray tube and a flat panel detector. Alternatively, the imaging apparatus may include two X-ray tubes and two flat panel detectors, and beams emitted from the two X-ray tubes intersect. Of course, the imaging apparatus may also be a combination of any two or more different imaging apparatuses. For example, the imaging apparatus may be a combination of the X-ray imaging apparatus and the DSA imaging apparatus. The present disclosure does not limit a specific setup mode of the imaging apparatus, and only uses the above imaging apparatus as an example to make an exemplary description.

Specifically, when the imaging apparatus includes an imaging center point, the common focus coincides with the imaging center point.

As shown in FIG. 8, the imaging apparatus 23 may be a bulb tube 232 and a flat panel detector 231 separately provided with a fixing device to fix the imaging apparatus 23, or the imaging apparatus 23 may also be separately provided with a driving apparatus to drive the bulb tube 232 and the flat panel detector 32 to rotate. Alternatively, as shown in FIG. 9, the imaging apparatus 23 may be fixedly arranged in a shielding apparatus 24, the specific position and structure of the shielding apparatus 24 are not limited in the present disclosure, and the above shielding apparatus is used as an example to make an exemplary description.

In addition, the radiotherapy device further includes a treatment couch 22 for carrying a patient. As shown in FIG. 7-FIG. 10, the present disclosure does not limit the specific structure or movement form of the treatment couch 22, which may be a three-dimensional couch as shown in FIG. 8-FIG. 10, or may be a six-dimensional couch as shown in FIG. 7. The treatment couch 22 may be selectively configured according to treatment needs, and related details are omitted herein.

In the radiotherapy device provided by the present disclosure, an anti-sinking component is also arranged between the collimator and the source body. Referring to FIG. 7 to FIG. 8, the anti-sinking component is a bearing.

In the radiotherapy device provided by the present disclosure, the radioactive source apparatus further includes a shielding apparatus 24. The shielding apparatus 24 is located on a side of the radioactive source apparatus 21. Beams emitted from the radioactive source 211a are shielded by the shielding apparatus 24 after passing through the common focus f. For example, as shown in FIG. 8-FIG. 10, the shielding apparatus 24 is located at a side of the common focus f of the radioactive source apparatus 21, and the beams emitted from the radioactive source 211a are shielded by the shielding apparatus 24 after passing through the common focus f, so as to avoid excessive radiation in a treatment room. For example, if the shielding apparatus 24 is shaped like an annular body, all the rays from the radioactive source 211a rotating about the central axis are received by the shielding apparatus. Alternatively, the shielding apparatus 24 is a shielding block that can rotate along the central axis of the radioactive source apparatus 21 to follow the radioactive source 211a to rotate so as to receive the rays after passing through the common focus f. It is to be noted that when the treatment couch 22 carries the patient to move, the shielding apparatus 24 is provided with a channel to facilitate the movement of the treatment couch.

The collimator in the present disclosure is specifically introduced and described below.

The present disclosure provides a collimator applied to a radiotherapy device. The radiotherapy device includes a plurality of radioactive sources, a plurality of collimating hole groups are arranged on the collimator, and an angle range of each collimating hole group in the longitude direction is within a preset angle range. Each of the collimating hole groups includes a plurality of collimating holes, and beams emitted from the plurality of radioactive sources intersect at a common focus after passing through each collimating hole of the collimating hole group.

As shown in FIG. 5, the collimator 212 may be bowl-shaped, and the longitude direction of the collimator 212 is as shown by arrow j1 in FIG. 5, which is 0°-360° in the longitude direction. The collimator may also be tube-shaped as shown in FIG. 6, and the longitude direction of the collimator is the direction as shown by arrow j2 in FIG. 6. Both ends of the cylinder in FIG. 6 may have equal size, or of course, may have different sizes (as shown in FIG. 10). The present disclosure does not limit the specific shape of the collimator, and the longitude direction in the present disclosure is described only taking the above shapes as examples.

For example, as shown in FIG. 5, the present disclosure provides a collimator 212. The collimator in FIG. 5 is provided with four collimating hole groups as an example, i.e., No. 1 collimating hole group (502), No. 2 collimating hole group (504), No. 3 collimating hole group (506), and No. 4 collimating hole group (508). Each collimating hole group includes 24 collimating holes respectively as an example. Taking the No. 1 collimating hole group (502) as an example, beams emitted from the plurality of radioactive sources intersect at a common focus after passing through each collimating hole of the No. 1 collimating hole group. The angle range of the No. 1 collimating hole group, the angle range of the No. 2 collimating hole group (504), the angle range of the No. 3 collimating hole group (506), and the angle range of the No. 4 collimating hole group (508), in the longitude direction are within the preset angle range. In FIG. 5, the No. 1 collimating hole group is taken as an example, and the angle range of the No. 1 collimating hole group in the longitude direction (the circular direction parapedicular to the central axis (202) as shown by arrow j1 in FIG. 5) is denoted as A. As an example, the preset angle range A may be between 5° and 60°, i.e., 5° 60°. The preset angle range A may be any angle range between 5° and 60°. As an example, the preset angle range A may be 5°, 8°, 10°, 12°, 18°, 20°, 25°, 30°, 40°, 45°, 50°, or 60°.

For the collimator provided by the present disclosure, in the longitude direction, a pitch between two adjacent collimating holes is larger than a size of the radioactive source. Furthermore, the collimator may misalign the radioactive source by a smaller angle, such that the radioactive source can be shielded by a pitch between the collimating holes instead of by a shield. Therefore, the radioactive source can be quickly turned on or off.

For example, for the collimator provided by the present disclosure, in the longitude direction, each collimating hole group a plurality of rows of radioactive sources, and the angle range between two adjacent rows of radioactive sources ranges from 2° to 15°. For example, among the plurality of collimating hole groups, the angle between any two adjacent rows of collimating hole groups is the same, or the angles between two adjacent rows of different collimating hole groups are different, which is not limited in the present disclosure, and what is shown in FIG. 5 is just an exemplary description. As shown in FIG. 5, the plurality of radioactive sources are divided into four rows, taking an example where the angle range between adjacent rows of collimating holes is B (in FIG. 4, two rows are taken as an example), the angle range B may range from 2° to 15°, i.e., 2°≤B≤15°, and the preset angle range B may be any angle range from 2° to 15°. For example, the preset angle range B may be 2°, 2.5°, 3°, 5°, 6°, 8°, 10°, 12°, or 15°.

For the collimator provided by the present disclosure, the angle range between the collimating hole groups in the latitude direction is from 20° to 60°. For example, as shown in FIG. 5, a preset angle range C may be between 20° and 60°, i.e., 20°≤C.≤60°, and the preset angle range C may be any angle range in the from 20° to 60°. For example, the preset angle range C may be 20°, 25°, 30°, 38°, 40°, 45°, 50°, 53°, or 60°.

For example, in the collimator provided by the present disclosure, in the latitude direction, the angle range between any two adjacent collimating holes is from 1° to 10°. For example, the angle range between any two adjacent collimating holes in the latitude direction is the same, or the angle range between any two adjacent collimating holes in the latitude direction is different, which is not limited in the present disclosure, and the above example as shown in FIG. 5 merely serves as an exemplary description. For example, as shown in FIG. 5, taking two collimating holes as an example, an angle range between the two collimating holes in the latitude direction is denoted as D, the angle range D may range from 1° to 10°, i.e., 1° A≤D≤10°, and the preset angle D may be any angle range in the range of from 1° to 10°. For example, the preset angle range D may be 1°, 2°, 3°, 5°6°, 8°, 9°, or 10°.

[61] For the collimator as shown in FIG. 5, an example is taken where the collimating holes of each collimating hole group are classified into a plurality of rows in the longitude direction and the radioactive sources in the same row have the same longitude, and the collimating holes of each collimating hole group are classified into a plurality of rows in the latitude direction and the radioactive sources in the same row have the same latitude. Further, to implement non-coplanar radiation and to better protect normal tissues, in the source body provided by the present disclosure, the collimating holes have different positions in the latitude direction. That is, each collimating hole has different latitudes.

The collimator is provided with a plurality of collimating hole groups. For example, the collimator may be provided with two or more collimating hole groups. In FIG. 5, an exemplary description is made by taking an example where the collimator is provided with four collimating hole groups. Each collimating hole group includes a plurality of collimating holes, and the number of the plurality of collimating holes corresponding to the radioactive sources may range from 20 to 180, for example, 30 or 180. The present disclosure does not limit the number or arrangement of the collimating holes, and the example as shown in FIG. 5 merely serve as an exemplary description. The radiotherapy device also includes a plurality of radioactive sources, and the collimating holes on the collimator correspond to the radioactive sources in number and arrangement, such that the beams emitted from the radioactive sources intersect at a common focus after passing through the collimating holes.

For example, as shown in FIG. 6, the collimator also may be tube-shaped as shown in FIG. 6, and the longitude direction of the collimator is the direction as shown by arrow j2 in FIG. 6. Both ends of the cylinder in FIG. 6 have equal size, or of course, may have different sizes (as shown in FIG. 10). The present disclosure does not limit the specific shape of the source body, and the shapes as shown in FIG. 5 and FIG. 6 serve as examples. An exemplary description is made in FIG. 6 by taking an example where the collimator is provided with two collimating hole groups and each collimating hole group includes 20 collimating holes.

The collimator 212 provided by the present disclosure also includes a shield region 2121 configured to shield the beams emitted from the plurality of radioactive sources. That is, the radioactive sources may be turned off by shielding rays from the radioactive sources with the collimator. The present disclosure does not limit the specific position of the shield region in the shield body. In FIG. 5, an exemplary description is made by taking an example where the shield region is spatially opposite to each collimating hole group.

For example, in the collimator provided by the present disclosure, the shield region is located between any two adjacent collimating hole groups among the plurality of collimating hole groups. For example, as shown in FIG. 11, an exemplary description is made by taking an example where the shield region is located between the No. 2 collimating hole group and the No. 3 collimating hole group.

Figure 11:
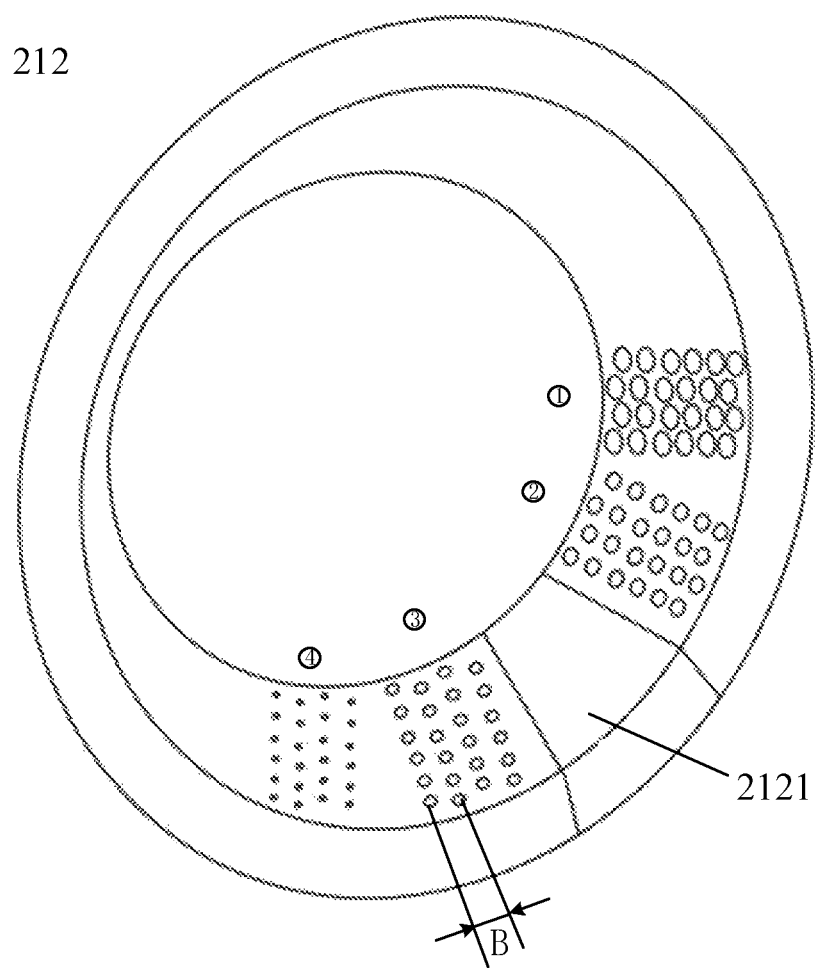
FIG. 11 is a schematic diagram of still another collimator according to an embodiment of the present disclosure.

In FIG. 11, an example is made where only one shield region is included. The present disclosure provides a collimator, which includes a plurality of shield regions. For example, the shield region may also be arranged between the No. 1 collimating hole group and the No. 2 collimating hole group. Alternatively, the shield region may also be arranged between the No. 3 collimating hole group and the No. 4 collimating hole group. Alternatively, the shield region may also be arranged between any two adjacent collimating hole groups. The present disclosure does not limit the number and distribution of the plurality of shield regions, and merely uses the above example to make an exemplary description.

The collimator provided by the present disclosure includes an internal collimator and an external collimator which are fixedly connected to one another, and a collimating hole on the internal collimator and a collimating hole on the external collimator are correspondingly arranged. That is, the collimator may include a double layer, and the internal collimator and the external collimator may be fixed through screw fastening.

The collimator provided by the present disclosure includes an internal collimator and an external collimator, which can rotate with respect to each other. For example, during the treatment, if an accident occurs, the radioactive source can be turned off quickly through the internal collimator, and then the external collimator is rotated to align the shield with the radioactive source to shield the radioactive source. Furthermore, the shield region of the internal collimator is aligned with the radioactive source, such that the radioactive source can be turned off completely.

For the collimator provided by the present disclosure, the collimating hole on the internal collimator is a taper hole, and/or the collimating hole on the external collimator is a straight hole. For example, the internal collimator and the external collimator each may be provided with a straight hole; or the internal collimator is provided with a taper hole, whereas the external collimator is provided with a straight hole; or the internal collimator and the external collimator each may be provided with a taper hole.

For the collimator provided by the present disclosure, the shield region is provided with a shield body, and a material density of the shield body is greater than that of the collimator. For example, the shield body is fixedly connected to the collimator, and the shield body may be formed by a tungsten block or a lead block or an alloy thereof. The collimating may be formed by cast iron. Thus, the shield body can better shield the radioactive source.

Figure 12:
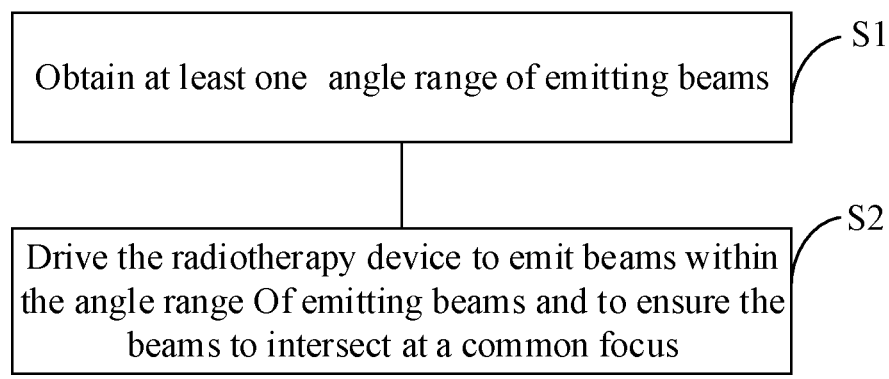
FIG. 12 is a schematic diagram of a control driving method according to an embodiment of the present disclosure.

The present disclosure provides a control driving method for a radiotherapy device. As shown in FIG. 12, the control driving method includes:

Step S1: obtaining at least one angle range of emitting beams; and

Step S2: driving the radiotherapy device to emit beams within the at least one angle range of emitting beams and to ensure the beams to intersect at a common focus.

Figure 13:
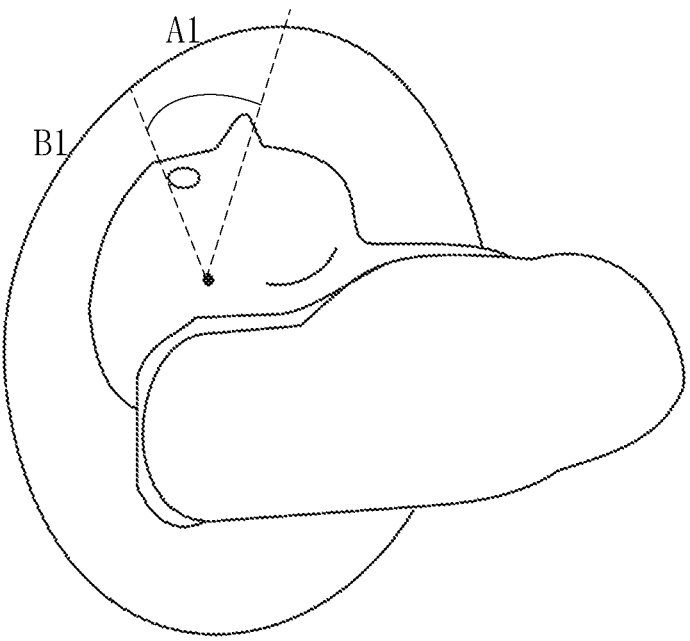
FIG. 13 is a schematic diagram of a treatment irradiation according to an embodiment of the present disclosure.

It is to be noted that a preset zero position is generally set for the driving apparatus in the radiotherapy device, and the zero position serves as a reference during the radiation treatment to confirm to drive within a drive angle range. In the present disclosure, the angle range of emitting beams may be an angle range required for the radiotherapy device to emit beams for radiation treatment, wherein the angle range is included in a corresponding treatment plan worked out by a physician according to a tumor image of a patient, and the angle range is an angle range for the driving apparatus to drive. For example, as shown in FIG. 13, in the corresponding treatment plan worked out by the physician according to the tumor image of the patient, the radiotherapy device performs a radiation treatment in a 81 interval, but does not perform the radiation treatment in an A1 interval (an A1 region includes radiation regions of two eyes to prevent rays from causing damage to optic nerves). The angle range of emitting beams is a drive angle range where the driving apparatus drives the radioactive source to radiate in the B1 interval, and a protection angle range is a drive angle range where the driving apparatus drives the radioactive source not to radiate in the A1 interval. During the radiation treatment, it is only necessary to rotate to irradiate within the drive angle range of the irradiation in the B1 interval, such that sensitive tissues may be prevented from damaging due to irradiating the eyes. For example, the drive angle range is a rotation angle of the motor. In the present disclosure, if the radiotherapy device rotates more than 360°, the drive angle range also exceeds 360°. Alternatively, if the radiotherapy device rotates more than 360°, the number of rotations and the drive angle range corresponding to different numbers of rotations are demarcated.

Of course, during the radiation treatment, rotatory irradiation may also be performed on the A1 region and the B1 region. In this case, the angle range of emitting beams is the drive angle range for irradiation in the A1 interval and the B1 region. For example, the angle range of emitting beams may be 360°. At this moment, irradiation dosage of sensitive tissues such as the optic nerves may be reduced by reducing irradiation time to protect the sensitive tissues and organs.

According to a control driving method provided by the present disclosure, a radiotherapy device includes a plurality of radioactive sources, and source points of the plurality of radioactive sources are within a preset angle range in a longitude direction. The control driving method includes: obtaining at least one angle range of emitting beams; and driving the radiotherapy device to emit beams within the angle range of emitting beams and to ensure the beams to intersect at a common focus, such that sensitive tissues and organs such as eyes can be protected from extra damage during the treatment of head tumors.

Figure 14:
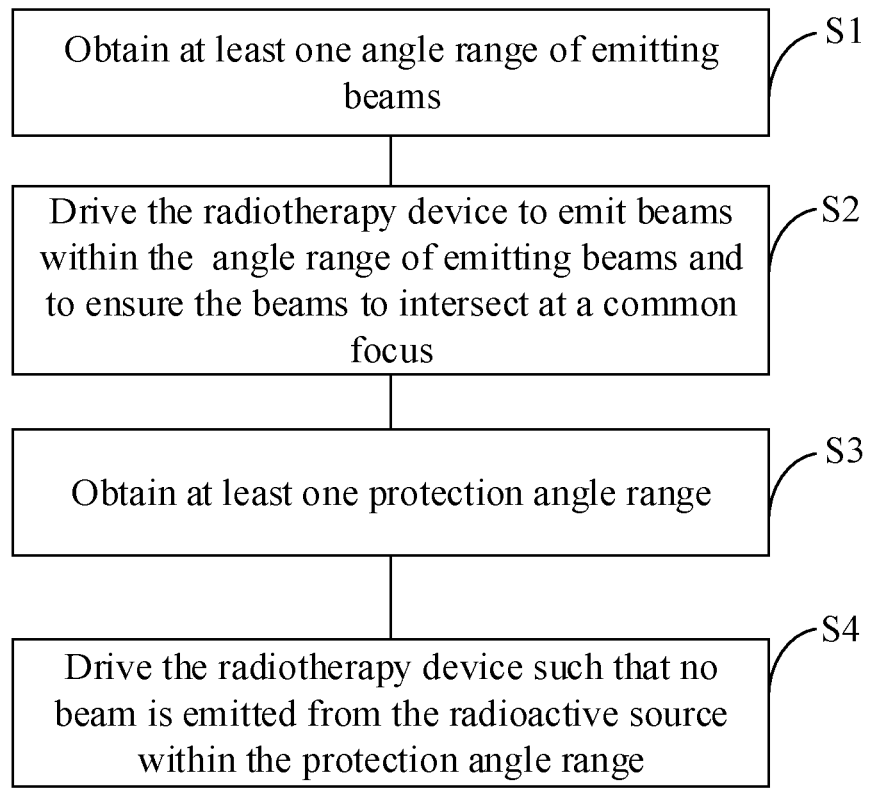
FIG. 14 is a schematic diagram of another control driving method according to an embodiment of the present disclosure.

As shown in FIG. 14, the control driving method provided by the present disclosure further includes:

Step S3: obtaining at least one protection angle range. The at least one protection angle range is less than 360°.

Figure 15:
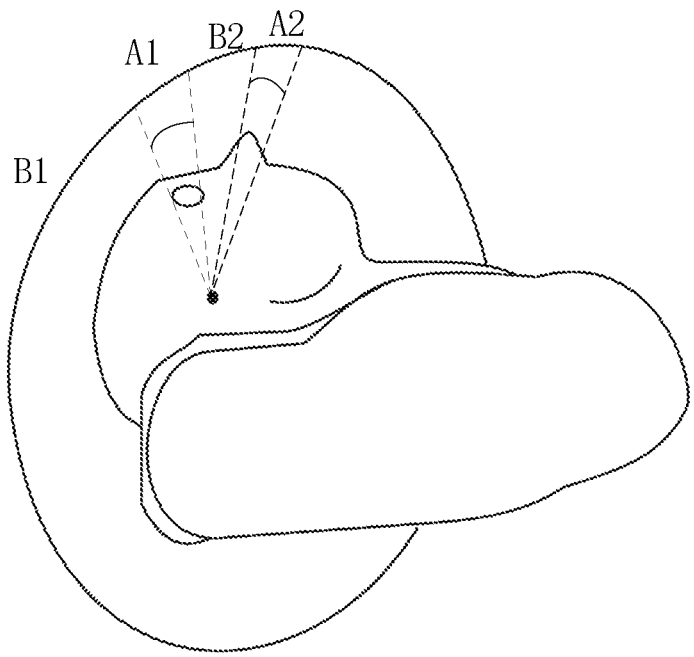
FIG. 15 is a schematic diagram of another treatment irradiation according to an embodiment of the present disclosure.

As shown in FIG. 15, the radiotherapy device performs a radiation treatment in a B1 interval and a B2 interval, but does not perform the radiation treatment in an A1 interval and an A2 interval (the A1 interval and the A2 interval correspond to eye regions to prevent rays from causing damage to optic nerves). The angle range of emitting beams is a drive angle range where the driving apparatus drives the radioactive source to radiate in the B1 interval and the B2 interval, and the protection angle range is a drive angle range where the driving apparatus drives the radioactive source not to radiate in the A1 interval or the A2 interval.

Step S4: driving the radiotherapy device such that no beam is emitted from the radioactive source within the protection angle range.

According to a control driving method provided by the present disclosure, a radiotherapy device includes a plurality of radioactive sources, and source points of the plurality of radioactive sources are within a preset angle range in a longitude direction. The control driving method includes: obtaining at least one angle range of emitting beams and at least one protection angle range; and driving the radiotherapy device to emit beams within the angle range of emitting beams and to ensure the beams to intersect at a common focus, such that no beam is emitted from the radioactive sources within the protection angle range. In this way, during the treatment of head tumors, the sensitive tissues and organs such as eyes can be protected from extra damage.

For example, the at least one angle range of emitting beams is adjacent to the at least one protection angle range. As shown in FIG. 15, a radiation treatment is performed in the B1 interval and the B2 interval, but the radiation treatment is neither performed in the A1 interval nor performed in the A2 interval. Because the B1 interval is adjacent to the A1 interval, the angle range of emitting beams corresponding to the B1 interval is adjacent to the protection angle range corresponding to the A1 interval.

According to the control driving method provided by the present disclosure, a plurality of angle range of emitting beams are obtained, and the radiotherapy device has different speeds within the at least two angle range of emitting beams. For example, referring to FIG. 15, when the radiation treatment is performed in the B1 interval and the B2 interval, the angle range of emitting beams corresponding to the B1 interval and the angle range of emitting beams corresponding to the B2 interval are obtained. The speed of the radiotherapy device within the angle range of emitting beams corresponding to the B1 interval is denoted as V1, and the speed of the radiotherapy device within the angle range of emitting beams corresponding to the B2 interval is denoted as V2, V1V2. Radiation time at different positions may be adjusted by adjusting the speed, such that dosage of the focus is adjusted.

For example, as shown in FIG. 13, when a rotatory radiation is performed in the A1 region and the B1 region during the radiation treatment, the angle range of emitting beams is the drive angle range for radiation performed in the A1 region and the B1 region. The speed of the radiotherapy device within the angle range of emitting beams corresponding to the B1 interval is denoted as V1, and the speed of the radiotherapy device within the angle range of emitting beams corresponding to the A1 interval is denoted as V2, V1<V2. That is, the speed in the A1 interval is greater than the speed in the B1 interval, such that the dosage received by sensitive tissues in the A1 interval is reduced to protect the sensitive tissues and organs.

It is to be noted that the drive angle range in the present disclosure is the rotation angle of the motor, and the drive angle range also exceeds 360°. For example, if the rotation angle of the motor exceeds 360°, the number of rotations and the drive angle range corresponding to different numbers of rotations are demarcated. The radiotherapy device has different speeds within at least two angle range of emitting beams, and has different drive speeds in the same radiation interval corresponding to different numbers of rotations. For example, if planned treatment time for a radiation treatment is 2 min, and 1 min is required for per rotation of the motor, as shown in FIG. 15, the drive speed for radiation in the B1 region within the angle range of emitting beams of the first rotation is denoted as V1, and the drive speed for radiation in the B1 region within the angle range of emitting beams of the second rotation is denoted as V2, V1≠V2.

According to the control driving method provided by the present disclosure, for example, as shown in above figures, two angle range of emitting beams having different speeds are adjacent to each other.

According to the control driving method provided by the present disclosure, the radiotherapy device is driven to reciprocate within the angle range of emitting beams. For example, if only one angle range of emitting beams is obtained, the radiotherapy device may reciprocate within the angle range of emitting beams to increase the dosage received by a tumor. Of course, if a plurality of angle ranges of emitting beams are obtained, the radiotherapy device may also reciprocate within the angle ranges of emitting beams to increase the dosage received by the tumor.

According to the control driving method provided by the present disclosure, the shield body is provided with a shield region, Step S4 in FIG. 14 specifically includes: driving the radiotherapy device such that the beams emitted from the plurality of radioactive sources are shielded by the collimator. For example, the source body may be driven to misalign the collimator, such that the radioactive source on the source body is shielded by a pitch between the collimating holes on the collimator. A smaller angle of misaligned rotation is needed such that the source body misaligns the collimator, and thus the radioactive source can be quickly turned on or off. Alternatively, the source body may be driven to misalign the collimator, such that the radioactive source on the source body is shielded by the shield region on the collimator.

Figure 16:
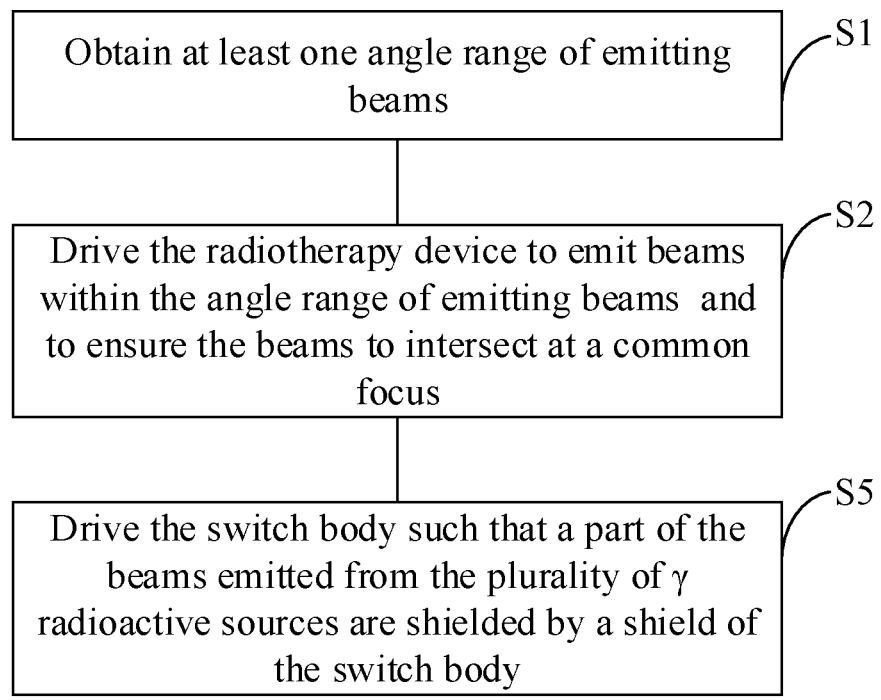
FIG. 16 is a schematic diagram of still another control driving method according to an embodiment of the present disclosure.

According to the control driving method provided by the present disclosure, when the radiotherapy device further includes a switch body, taking steps in FIG. 14 as examples, as shown in FIG. 16, the control driving method further includes:

Step S5: driving the switch body such that a part of the beams emitted from the plurality of y radioactive sources are shielded by a shield region of the switch body.

The switch body is as shown in FIG. 11. The switch body is driven such that a part of the beams emitted from the plurality of y radioactive sources are shielded by the shield region of the switch body. In this way, a part of the beams emitted from the radioactive sources may be shielded by the shield region of the switch body, thereby implementing the objective of regulating radiation dose.

According to the control driving method provided by the present disclosure, in the longitude direction, a pitch between two adjacent collimating holes in the same collimating hole group is larger than a size of the radioactive source. Step S4 in FIG. 14 specifically includes: driving the radiotherapy device such that the plurality of radioactive sources misalign with the collimating hole, wherein the beams emitted from a part of the radioactive sources are shielded by an edge region of the collimating hole group, and the beams emitted from the remaining radioactive sources are shielded by a pitch region between the collimating holes. For example, the source body may be driven to misalign the collimator, such that the radioactive sources on the source body are shielded by a pitch between the collimating holes on the collimator. A smaller angle of misaligned rotation is needed such that the source body misaligns the collimator, and thus radioactive sources can be quickly turned on or off.

Figure 17:
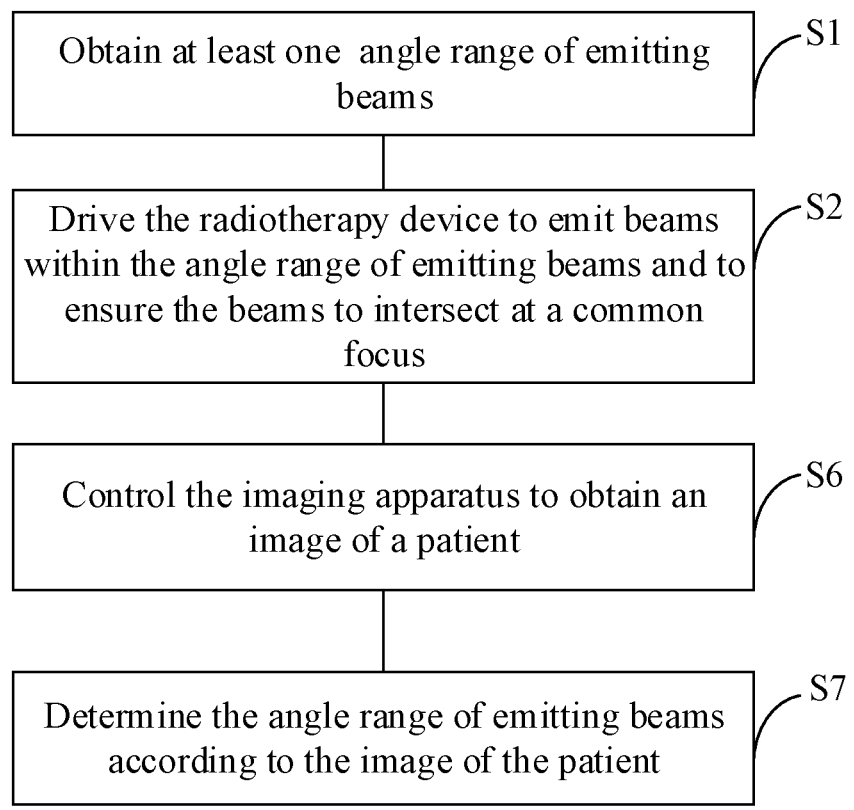
FIG. 17 is a schematic diagram of still another control driving method according to an embodiment of the present disclosure.

For example, in the radiotherapy device as shown in FIG. 8-FIG. 10, the common focus is located outside an end surface of the radioactive source apparatus. The radiotherapy device further includes an imaging apparatus, and the common focus is located within an imaging region of the imaging apparatus. As shown in FIG. 17, the control driving method also includes:

Step S6: controlling the imaging apparatus to obtain an image of a patient.

Step S7: determining the angle range of emitting beams according to the image of the patient.

It is to be noted that the angle range of emitting beams in Step S1 may be a angle range of emitting beams determined by a physician based on the image of the patient before the radiation treatment, and during the treatment, the angle range of emitting beams may be determined or adjusted based on the obtained image.

Figure 18:
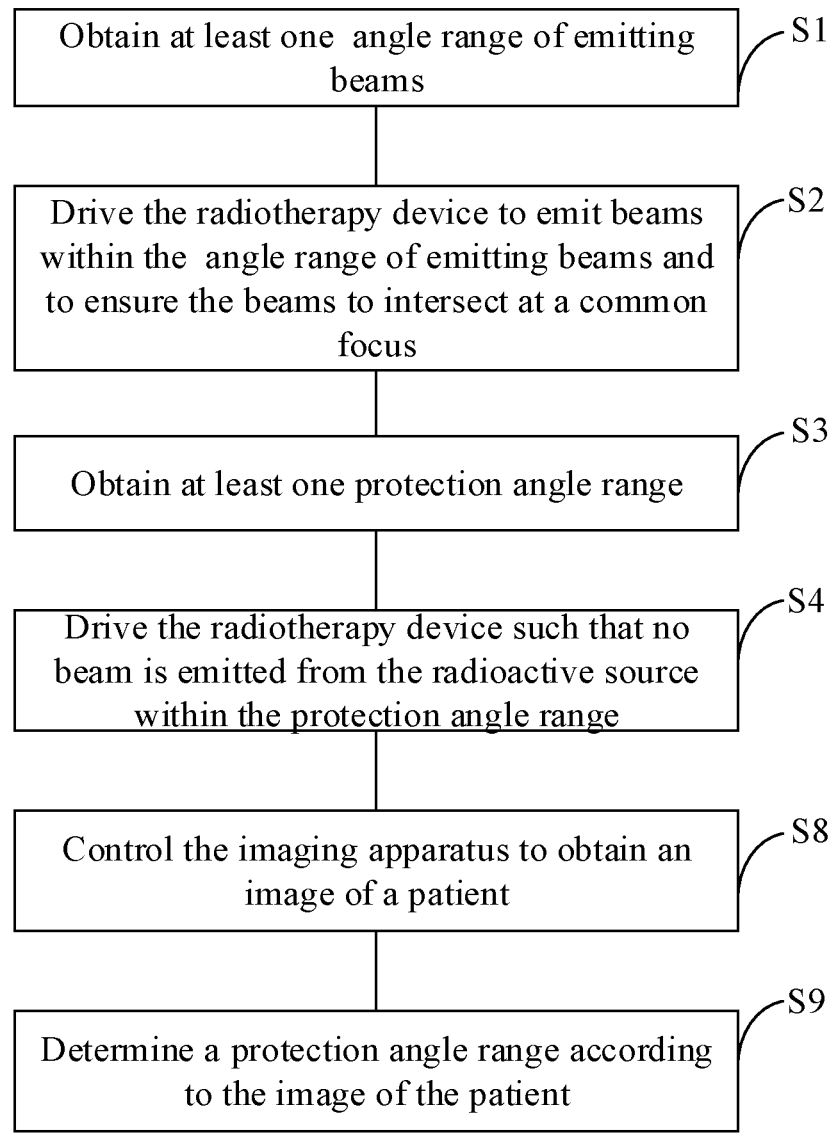
FIG. 18 is a schematic diagram of still another control driving method according to an embodiment of the present disclosure.

For example, the radiotherapy device as shown in FIG. 8-FIG. 10 further includes an imaging apparatus, and the common focus is located within an imaging region of the imaging apparatus. As shown in FIG. 18, the control driving method also includes:

Step S8: controlling the imaging apparatus to obtain an image of a patient; and

Step S9: determining a protection angle range according to the image of the patient.

Similarly, the protection angle range in Step S3 may be a protection angle range determined by the physician based on the image of the patient before the radiation treatment, and during the treatment, the protection angle range may be determined or adjusted based on the obtained image.

It is to be noted that in the control driving method provided by the present disclosure, the present disclosure does not limit sequences of the above steps, and merely uses the above examples to make an exemplary description.

The embodiments set forth above are only illustrated as alternative embodiments of the present disclosure, and are not intended to limit the present disclosure. All modifications, equivalent substitutions and improvements made within the spirit and principles of the present disclosure shall fall within the protection scope of the present disclosure.

What is claimed is:

1. A collimator comprising:
   a central axis; and
   a plurality of collimating hole groups located in a portion of the collimator such that each of the plurality of collimating hole groups is located within a preset angle range in a longitude direction,
   wherein the longitude direction is a circular direction perpendicular to the central axis and the portion has a maximum angle range of less than 180° in the longitude direction, and
   wherein each of the plurality of collimating hole groups comprises a plurality of collimating holes such that beams emitted from a plurality of radioactive sources surrounding the collimator intersect at a common focus after passing through the plurality of groups of collimating holes.

2. The collimator according to claim 1, wherein the maximum angle range is less than 90°.

3. The collimator according to claim 1, wherein the preset angle range is between 5° and 60°.

4. The collimator according to claim 1, wherein a distance between two adjacent collimating holes in a collimating hole group of the plurality of collimating hole groups in the longitude direction is larger than a size of a radioactive source of the plurality of radioactive sources emitting beams passing through the plurality of collimating holes.

5. The collimator according to claim 1, wherein the collimator further comprises a shield region configured to shield the beams emitted from the plurality of radioactive sources.

6. The collimator according to claim 5, wherein the shield region is located outside the portion.

7. The collimator according to claim 5, wherein the shield region is located between two collimating hole groups.

8. The collimator according to claim 1, wherein the collimator is bowl-shaped.

9. A radiotherapy device, comprising:
a radioactive source apparatus having a source body including a plurality of radioactive sources; and
a collimator comprising:
a central axis; and
a plurality of collimating hole located in a portion of the collimator such that each of the plurality of collimating hole groups of is located within a preset angle range in a longitude direction,
wherein the longitude direction is a circular direction perpendicular to the central axis and the portion has a maximum angle range of less than 180° in the longitude direction, and
wherein each of the plurality of collimating hole groups comprises a plurality of collimating holes such that beams emitted from the plurality of radioactive sources surrounding the collimator intersect at a common focus after passing through the plurality of groups of collimating holes.

10. The radiotherapy device according to claim 9, wherein the common focus is located outside an end surface of the radioactive source apparatus.

11. The radiotherapy device according to claim 9, further comprising: an imaging apparatus arranged at a side of the radioactive source apparatus, and the common focus is located within an imaging region of the imaging apparatus.

12. The radiotherapy device according to claim 11, wherein the imaging apparatus comprises at least one of X-ray imaging apparatus, a Computed Tomography (CT) imaging apparatus, an Magnetic Resonance (MR) imaging apparatus, a Digital Subtraction Angiography (DSA) imaging apparatus, an ultrasound imaging apparatus, or a Positron Emission Computed Tomography (PET) imaging apparatus.

13. The radiotherapy device according to claim 9, wherein the radioactive source apparatus further comprises a shielding apparatus located at a side of the radioactive source apparatus, and the beams emitted from the plurality of radioactive sources are shielded by the shielding apparatus after passing through the common focus.

14. A method for controlling a radiotherapy device, the radiotherapy device comprising a radioactive source apparatus having a source body including a plurality of radioactive sources; and a collimator comprising a central axis, and a plurality of collimating hole located in a portion of the collimator such that each of the plurality of collimating hole groups is located within a preset angle range in a longitude direction, wherein the longitude direction is a circular direction perpendicular to the central axis and the portion has a maximum angle range of less than 180° in the longitude direction, and wherein each of the plurality of collimating hole groups comprises a plurality of collimating holes such that beams emitted from the plurality of radioactive sources surrounding the collimator intersect at a common focus after passing through the plurality of collimating holes,
the method comprising:
obtaining an angle range for emitting the beams; and
driving the radiotherapy device to emit the beams within the angle range and to ensure the beams intersect at the common focus.

15. The method according to claim 14, further comprising:
obtaining a protection angle range; and
driving the radiotherapy device such that no beams are emitted from the plurality of radioactive sources within the protection angle range.

16. The method according to claim 15, wherein the radiotherapy device further comprises a shield region; and the driving the radiotherapy device such that no beam is emitted from the plurality of radioactive sources within the protection angle range further comprises:
driving the radiotherapy device such that beams emitted from the plurality of radioactive sources are shielded by the shield region.

17. The method according to claim 15, wherein a distance between two adjacent collimating holes in a collimating hole group of the plurality of collimating hole groups in the longitude direction is larger than a size of a radioactive source of the plurality of radioactive sources emitting beams passing through the plurality of collimating holes; and the driving the radiotherapy device such that no beams are emitted from the plurality of radioactive sources within the protection angle range further comprises:
driving the radiotherapy device such that the plurality of radioactive sources rotate about the central axis, misalign with the collimating holes, and are shielded.

18. The method according to claim 15, wherein the radiotherapy device further comprises an imaging apparatus; and the method further comprises:
controlling the imaging apparatus to obtain an image of a patient; and
determining the protection angle range according to the image of the patient.

19. The method according to claim 14, wherein the angle range is a first angle range, further comprising obtaining a second angle range for emitting the beams, and the radiotherapy device has different speeds within the first angle range and the second angle range of emitting beams.

20. The method according to claim 14, wherein the radiotherapy device further comprises an imaging apparatus, and the method further comprises:
controlling the imaging apparatus to obtain an image of a patient; and
determining the angle range for emitting the beams according to the image of the patient.

* * * * *